United States Patent
Kosaka

Patent Number: 5,721,433
Date of Patent: Feb. 24, 1998

[54] APPARATUS AND METHOD FOR ANALYZING PARTICLE IMAGES INCLUDING MEASURING AT A PLURALITY OF CAPTURING MAGNIFICATIONS

[75] Inventor: Tokihiro Kosaka, Hyogo, Japan

[73] Assignee: Toa Medical Electronics Co., Ltd., Hyogo, Japan

[21] Appl. No.: 552,675

[22] Filed: Nov. 3, 1995

[30] Foreign Application Priority Data

Nov. 4, 1994 [JP] Japan ................. 6-271453

[51] Int. Cl.$^6$ ........................... G01N 21/00
[52] U.S. Cl. ........................... 250/573; 356/335
[58] Field of Search ............. 250/573, 574, 250/576; 356/335, 336

[56] References Cited

U.S. PATENT DOCUMENTS

5,159,403  10/1992  Kosaka ........................... 356/73
5,166,537  11/1992  Horiuchi et al. ............. 250/573
5,426,499  6/1995  Kosaka et al. ............... 356/39

Primary Examiner—Edward P. Westin
Assistant Examiner—Kevin Pyo

[57] ABSTRACT

An apparatus for analyzing particle images includes a sheath flow cell for transforming a particle suspension flow into a flat flow surrounded by a sheath liquid, a light source for irradiating particles in the transformed particle suspension flow, a video camera for capturing particle images of irradiated particles, an image analyzer for analyzing the captured particle images, and a display device. The image analyzer including a calculator for measuring a projected area and perimeter of each captured particle image to calculate a particle diameter and circularity of each particle, a graph making device for making a histogram based on the particle diameter and for making a scattergram based on two parameters corresponding to the particle diameter and the circularity to allow the display device to display the histogram and the scattergram, a memory for storing each of the captured particle images, and a particle image recalling device for allowing the display device to collectively display the particle images stored by the memory.

24 Claims, 9 Drawing Sheets

APPARATUS AND METHOD FOR ANALYZING PARTICLE IMAGES INCLUDING MEASURING AT A PLURALITY OF CAPTURING MAGNIFICATIONS

BACKGROUND OF THE INVENTION

1. Field of the Invention

The present invention relates to a particle image analyzing apparatus for obtaining information on particle size and shape parameter (or index) by capturing images of particles in a liquid and subjecting the particle images to image analysis as well as storing and displaying the particle images.

2. Related Art

In controlling powder quality of fine ceramic particles, toners, pigments, cosmetic powders, and the like, it is of great importance to measure and control their particle diameter and shape. Measuring apparatuses employing the liquid phase sedimentation method or electric detection zone method (Coulter method) are well-known and recently a measuring apparatus employing the laser diffraction scattering method is widely used.

However, the measurement precision (accuracy) is still not satisfactory enough in any of the measuring apparatuses employing the above methods. Particularly, when the particles to be measured are flat or oblong, the obtained particle diameters may possibly vary greatly depending on the measuring method employed. Generally, minute particles tend to aggregate during measurement. In such a case, it is not possible to get a precise particle size distribution, either. Also, it is difficult to obtain information on sphericity (circularity) or degree of aggregation of particles by use of the above conventional apparatuses for measuring the particle size distribution.

Among particles in suspension, large particles sediment faster than small particles, so that the particle concentration varies depending on time and space. The liquid phase sedimentation light transmittance method which is representative as a sedimentation method detects this variation by measuring the amount of transmitted light, whereby the particle size distribution is obtained. According to this sedimentation method, sedimentation velocity of particles having the same volume and density varies depending on the shape of the particles. Also, the aggregated particles sediment faster.

The apparatus employing the electric detection zone method detects the change of electric resistance which occurs when the particles, drifting in electrolytic solution, pass through a small hole. In this method, the volume equivalent diameter of each particle can be measured almost independent of its shape. Conversely speaking, it is difficult to obtain information on particle shape by the electric detection zone method. Moreover, since the area of electric detection region is considerably large in particle size, it is impossible to get a precise particle size distribution when the particles are aggregated or near to each other.

The apparatus now widely used employing the laser diffraction scattering method estimates and calculates the particle size distribution by use of information on the distribution of diffracted and scattered light intensities obtained by applying a laser light to a group of drifting particles based on the MIE scatter theory. This method is advantageous because it is possible to obtain, in one measurement, a particle size distribution for particles having diameters of 0.1 μm to several hundred μm with good reproducibility even when the sample to be measured contains particles of unknown sizes or is a mixture of particles with the same refractive index.

However, the apparatus employing the above method involves problems such as the following.

1) The intensity of light scattered by particles is greatly affected by the difference in shape, refractive index, surface condition and the like, so that it is difficult to obtain a precise particle size distribution.

2) It is necessary to use the precise refractive index of the particles to be measured, but particles having oxidized surface or impurities mingled with the particles sometimes make it difficult to obtain a correct particle size distribution by using well-known values.

3) The particle size distribution is deduced by solving simultaneous equations regarding the intensity distribution of light diffracted and scattered by many particles on the supposition that the particles are spherical, having smooth surfaces, and not aggregated. As to the particles that do not satisfy the above supposition, the simultaneous equations might not be sufficiently solved, necessitating specific corrections.

4) Due to specific corrections such as above, measurement may possibly cause great difference of results depending on the machines employed in the measurement.

As described above, the conventional measuring apparatuses are greatly affected by the shape or aggregation of particles, so that it is difficult to obtain a precise particle size distribution. Also, it is hard to obtain information on the shape of particles or the degree of aggregation.

Another method for measuring the shape of particles involves a combination of a microscope and an image processing apparatus. However, powders for industrial purposes are often made by crushing, so that one sample of such powders may possibly contain particles of considerably different sizes, making it impossible for the microscope to bring into focus all the particles on a slide glass. In other words, when the smaller particles are brought into focus, the larger particles do not come into focus. When the larger particles are brought into focus, the smaller particles do not come into focus. Therefore, this microscopic method can be employed only when the particles are approximately of equal size.

Further, in order to analyze thousands of particle images by this microscopic method, it is necessary to capture and analyze hundreds of images while shifting the slide glass little by little so as to change the field of view. This consumes a lot of time and labor. Due to the above reasons, measurement of particle size and shape by use of particle images is not so often conducted in the case of powders for industrial purposes.

SUMMARY OF THE INVENTION

The present invention provides an apparatus for analyzing particle images including a sheath flow cell for transforming a flow of particle suspension into a flow surrounded by a sheath liquid, an irradiator for irradiating particles in the transformed particle suspension flow with a light, an image capturing section for capturing particle images of the irradiated particles, an image analyzing section for analyzing the captured particle images, and a display. The image analyzing section provides a calculating unit for measuring a projected area and perimeter of each captured particle image to calculate a particle diameter and circularity of each particle, a graph making unit for making a histogram based on particle size frequency data corresponding to the particle diameters, for making a scattergram based on two parameters corresponding to the particle diameter and the circularity, and for allowing the display to display the histogram and the scattergram, a storage medium for storing each captured particle image, and particle image recalling section for allowing the display to collectively display the particle images stored by the storage medium.

DESCRIPTION OF THE PREFERRED EMBODIMENTS

The objects to be analyzed by the apparatus of the present invention include (1) inorganic particles such as fine ceramic powders, toners, pigments, and cosmetic powders, (2) organic particles such as plastic particles and food additives, (3) solid components contained in a living body such as cells, blood cells, and urine sediments, and (4) microorganisms such as planktons. They may be particles preliminarily processed by a dyeing treatment with dyes or labelling reagents. Particle diameter that can be measured by the apparatus is in the range of about 1 to 400 µm.

The sheath flow cell to be used is a cell capable of transforming a particle suspension flow, namely a sample liquid that contains particles, into a narrow or flat flow through hydrodynamic effect by surrounding the suspension flow with a sheath liquid. A conventionally known sheath flow cell may be used.

It is preferable to select a kind of sheath liquid to be supplied to the sheath flow cell depending on the properties of the particle suspension (properties of the particles and the solvent).

Preferably, the irradiator means is a stroboscope or a laser light source that emits a pulsed light. A light source that continuously emits light can be used, but in such a case a shutter has to be provided in the image capturing. The image capturing may be a video camera capable of capturing ordinary two-dimensional images.

The irradiator and the image capturing section are disposed opposite to each other with the sheath flow cell inbetween. If the particle suspension flow is transformed into a flat flow in the sheath flow cell, the irradiator preferably applies light perpendicularly to a flat surface of the particle suspension flow, the image capturing section being preferably disposed on its optical axis.

The image analyzing section is preferably provided with an image processing circuit of pipeline processing type capable of processing, by real time, screen images obtained every 1/30 second and a micro computer comprising a CPU, a ROM, a RAM, and an I/O port.

The display may be a CRT, a liquid crystal display, or the like.

The sheath flow cell allows particle suspension flow to be surrounded by sheath liquid and transforms it into a narrow or flat flow. The irradiator means applies light to the transformed suspension flow. The image capturing section captures images of the irradiated particles. The image analyzing means analyzes the captured particle images, the results thereof being displayed together with the particle images by the display.

Here, in the image analyzing section, the calculating unit measures the area and perimeter of each of the captured particle images and calculates particle diameter and circularity from particle data obtained by the measurement. The graph making unit makes a histogram based on the frequency data of the particle diameter and a two-dimensional scattergram on two parameters corresponding to the particle diameter and the particle circularity, allowing the display to display the histogram and the two-dimensional scattergram.

The storage medium stores each of the captured particle images. The particle image recalling unit allows the display to collectively display the particle images stored in the storage medium.

Namely, according to the particle analyzing apparatus, the size and perimeter of the particle can be obtained from each of the captured particle images. Also, the real morphological feature and aggregation state of the particles can be confirmed through the collectively displayed particle images.

Specifically described, the particle suspension is introduced into a transparent flow cell to be transformed into a narrow or flat flow. With the flow irradiated, the images of the particles in the flow are captured by a video camera. The projected area and the perimeter of each of the captured particle images are calculated and then the particle diameter and the circularity are calculated. Further, a histogram on particle size based on the particle diameter and a two-dimensional scattergram of the particle diameter and the circularity are made.

It is possible to obtain information on the particle circularity and the degree of aggregation by evaluating and confirming this two-dimensional scattergram and the real particle images.

EXAMPLES

The present invention will now be described by way of examples shown below. However, they are not intended to limit the scope of the invention.

Figure 1:
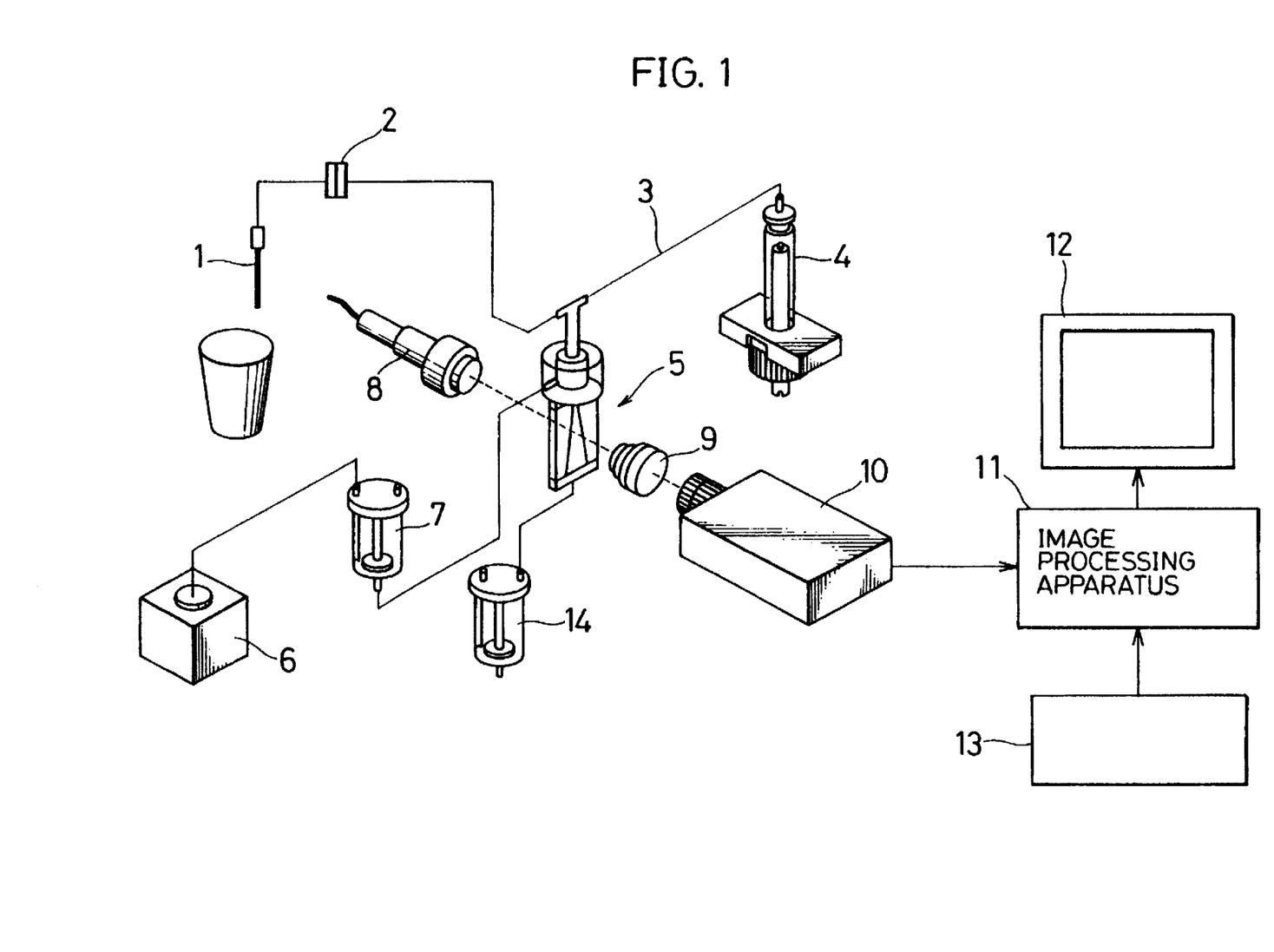
FIG. 1 is an explanatory view showing construction of an embodiment of the present invention.
Figure 2:
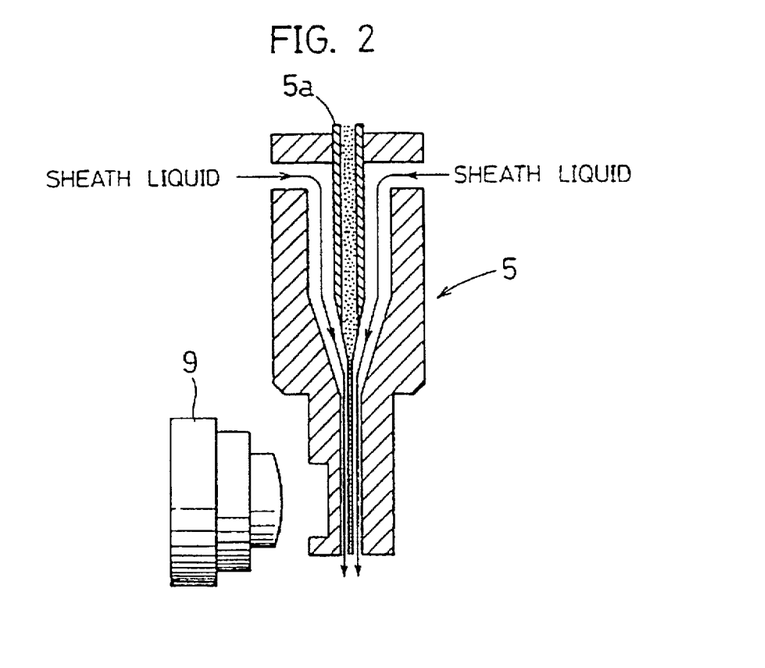
FIG. 2 is an enlarged sectional view of the principal part of FIG. 1.

FIGS. 1 and 2 show an example of particle image analyzing apparatus of flow method type according to the present invention. First, particle suspension is sucked through a suction pipette 1 by a suction means (not shown) such as a diaphragm pump and then is drawn through a sample filter 2 into a sample charging line 3 above a flow cell 5, as shown in these figures. The sample filter 2 removes oversize particles and dusts in the suspension so as not to clog the flow cell 5 having a narrow passageway. The sample filter 2 also serves to unravel oversize aggregates.

When the particles to be measured are translucent, it is preferable to stain the particles with a suitable dye. Although not shown in FIG. 1, a dyeing liquid bottle may be provided within the apparatus and a reaction chamber may be added for dyeing the sucked sample with the dyeing liquid.

The particle suspension thus drawn into the charging line 3 is introduced into the flow cell 5 by the operation of a sheath syringe 4 and squeezed out little by little from the tip of a sample nozzle 5a. At the same time, a sheath liquid is introduced from a sheath liquid bottle 6 through a sheath liquid chamber 7 into the flow cell 5. The particle suspension is then surrounded by the sheath liquid and, being hydrodynamically flattened, flows through the flow cell 5 as shown in FIG. 2 to be discharged through an exhaust liquid chamber 14. By periodically irradiating the thus flattened suspension flow with pulsed light from a stroboscope 8 every 1/30 second, still images of the particles are captured through an object lens 9 by a video camera 10 every 1/30 second.

The solvent for suspending the particles may be suitably selected according to the particle properties (particle diameter and specific gravity).

Also, it is preferable to change viscosity and specific gravity of the sheath liquid in accordance with the suspension properties such as the viscosity and specific gravity of the solvent so as to securely flatten or narrow the suspension flow. Although not shown in FIG. 1, a mechanism may be added in which a plurality of sheath liquid bottles are provided for easily selecting the sheath liquid to be used according to the property of the sample for measurement.

By capturing images of the flat surface of the suspension flow by the video camera 10, one can acquire particle images over the entire capturing area of the video camera 10, thereby capturing images of a lot of particles in one capture. Also, it is possible to maintain an approximately constant distance between the barycenter (the center of gravity) of the particles to be captured and the capturing surface of the video camera 10, so that one can always capture particle images in focus irrespective of the size of particles. Moreover, flat particles and oblong particles tend to arrange themselves in order by a hydrodynamic effect, so that the characteristic parameters obtained by analyzing particle images have small differences, which lead to good reproducibility.

If the suspension flow is flat, the number of particle images captured by applying pulsed light for a plurality of times is determined by the capturing area of the video camera 10, the thickness of the sample flow, the number of particles per volume in the suspension flow, and the number of capturing times (the number of frames). For example, the number of captured particle images would be 3600 if the capturing area is 200 μm×200 μm, the thickness of the sample flow 5 μm, the particle concentration 10000/μl, and the number of capturing frames 1800 (capturing for 60 seconds).

The capturing area is determined by the magnification of image formation on the light-receiving surface of the video camera 10 and its size. As the magnification of the object lens 9 becomes larger, the capturing area will be smaller, but enlarged images of smaller particles can be captured. When the magnification of the object lens 9 is small, the capturing area will be large, which is suitable for capturing images of large particles. The present apparatus is adapted to allow selection or switching during measurement (not shown) of the magnification of the object lens 9, providing a wide measuring range of particle diameters.

Image signals from the video camera 10 are processed by an image processing apparatus 11 and displayed by the monitor television 12. Reference numeral 13 denotes a keyboard (or a mouse) for various operations.

Figure 5:
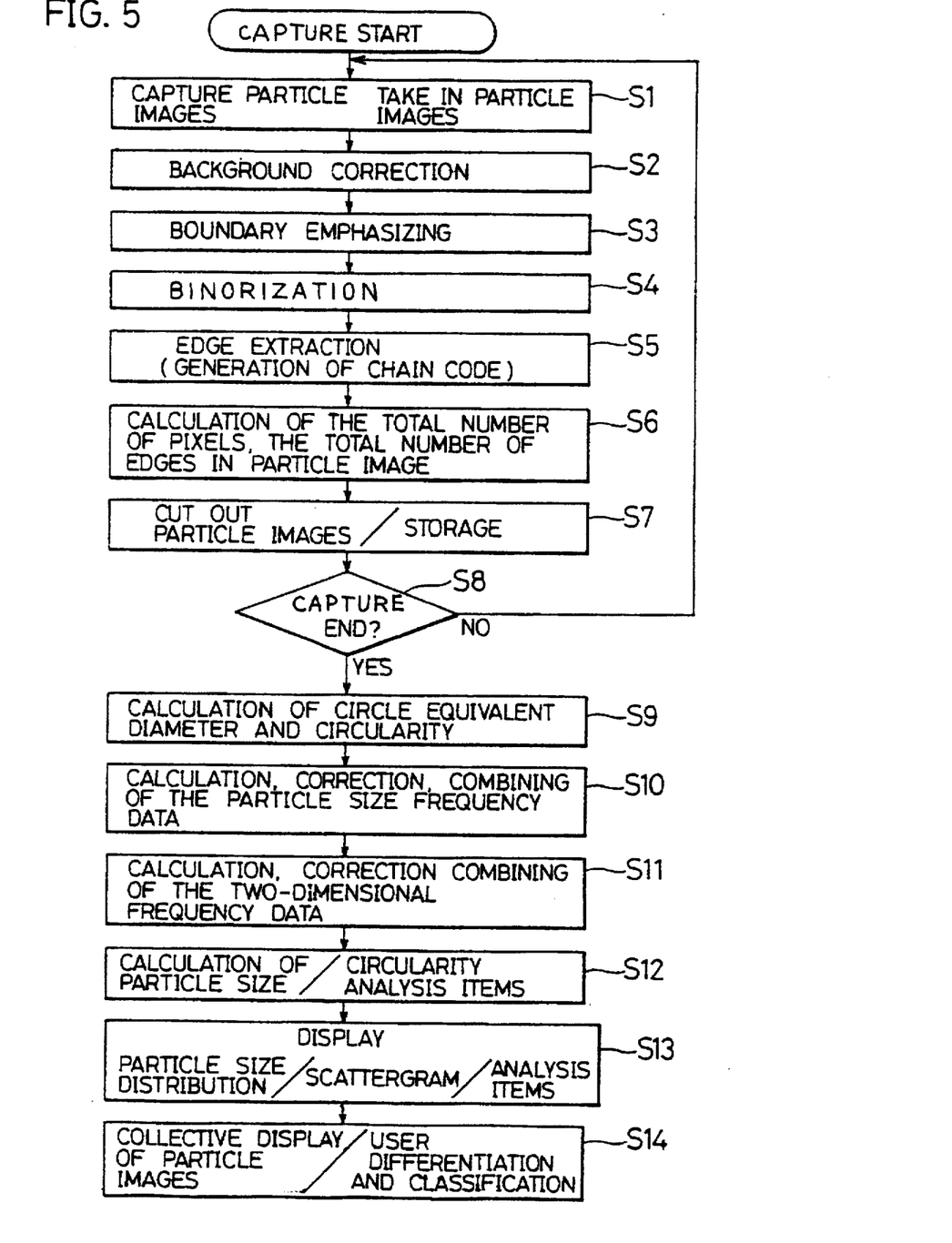
FIG. 5 is a flow chart showing processing procedures of the embodiment.

FIG. 5 shows procedures for processing particle images on screen captured every 1/30 second. Image signals are taken into the image processing apparatus 11 for A/D conversion as image data (step S1). First, a background correction is carried out to correct intensity irregularities (shading) of the light applied to the suspension flow (step S2).

Specifically, this is to take in, before the measurement, the image data obtained by applying light when the particles are not passing through the flow cell 5 and to operatively compare the image data with the image data of the real particle images on screen. This process is generally well-known as an image processing technique. Then, a process for emphasizing boundaries follows as a pretreatment for extracting precisely the boundaries of the particle images (step S3). Specifically, a generally well-known Laplacian emphasizing process is employed.

Next, the image data are digitized at a suitable threshold level (step S4). Then follows a process for determining whether the points in the digitized particle images are "edge points". With respect to each of the "edge points", a chain code, namely information on where (in what direction) the adjacent "edge points" are located, is generated (step S5). An edge tracing of the particle images is then carried out referring to the above chain code so as to obtain the total number of pixels, the total number of edges, and the number of oblique edges of each of the particle images (step S6).

By use of an efficient image processing apparatus capable of pipeline processing, one can execute the above image processing of screen images captured every 1/30 second in real time. The apparatus repeats the above image processing of a plurality of screen images captured at a certain magnification and then, through capturing images at a different magnification, executes a similar image processing. Also, particle images are cut out from the captured frames and stored in the image memory of the image processing apparatus 11 (step S7).

After capturing (step S8), the projected area S and the perimeter length L of each of the particle images are calculated according to the following formula using the total number of pixels, the total number of edges, and the number of oblique edges obtained for each of the particle images.

Figure 10:
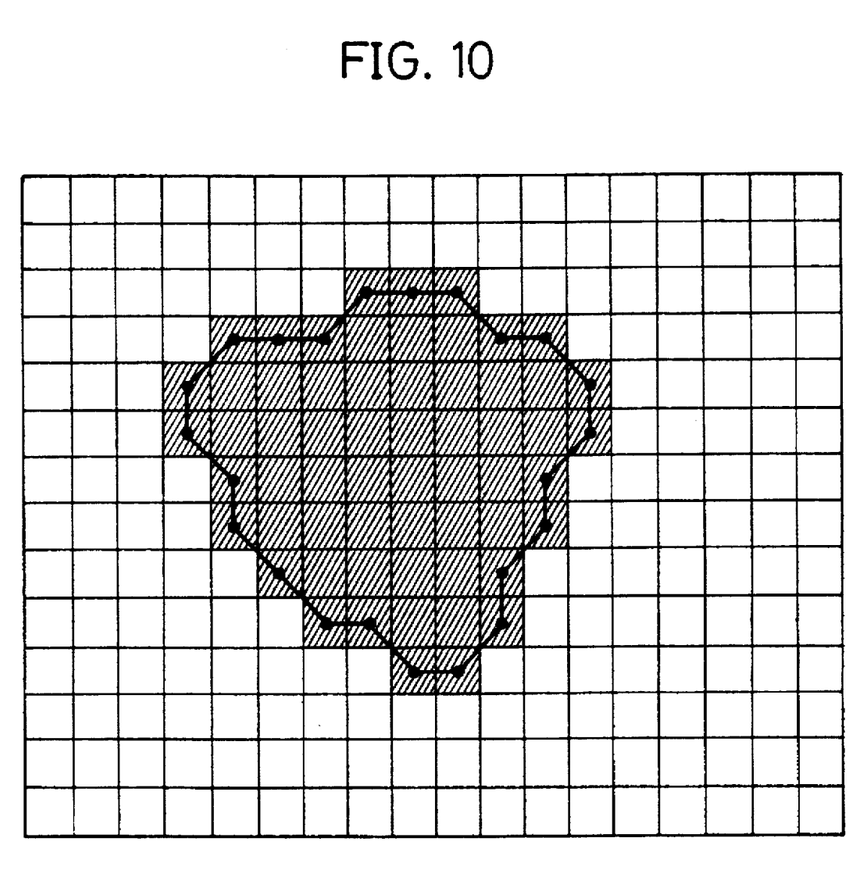
FIG. 10 is an explanatory view showing calculation of the area and perimeter of the captured particle images of the present invention.

Supposing the area of each pixel to be 1, the area S and the perimeter L of the frame obtained by connecting, as shown in FIG. 10, the centers of the edges located in the perimeter of the two-valued (digitized) images are represented by the following formula:

$$\text{Area } S = NP - (ND \times 0.5) - 1 \tag{1}$$

$$\text{Perimeter } L = (ND - NB) + (NB \times \sqrt{2}) \tag{2}$$

wherein NP, ND, and NB denote the total number of pixels, the total number of edges, and the number of oblique edges, respectively.

Next, the circle equivalent diameter and the circularity are calculated using the above area S and the perimeter L (step S9). To be exact, when the boundary of a particle image is drawn by using longitudinal and lateral lines and oblique lines of 45°, the perimeter length L as obtained by the above formula will be about 1.05 times larger than the real perimeter length in the case of circular particle images, necessitating a small correction in obtaining the circularity. The circle equivalent diameter of a particle image is a diameter of the circle having the same area as that of the projected particle image and is represented by the following formula (3). The circularity of a particle image is, for example, a value as defined by the following formula (4) and is equal to 1 when the particle image is a circle. As the particle image becomes more oblong, the circularity will be smaller.

$$\text{Circle equivalent diameter} = (AP/\pi)^{1/2} \times 2 \qquad (3)$$

$$\text{Circularity} = LC/LP \qquad (4)$$

wherein the AP, LC, and LP are the area of the projected particle image, the perimeter length of the circle having the same area as that of the projected particle image, the perimeter length of the particle image, respectively.

After the circle equivalent diameter of each of the particle images is calculated, the particle size frequency is counted based on the obtained circle equivalent diameters (step S10). Powders for industrial purposes are diverse and the particle diameter distribution extends in a very wide range. Therefore, the particle diameter is generally subjected to LOG (logarithm) conversion. The particle size frequency distribution is obtained by equi-partitioning the LOG-converted values.

Figure 3:
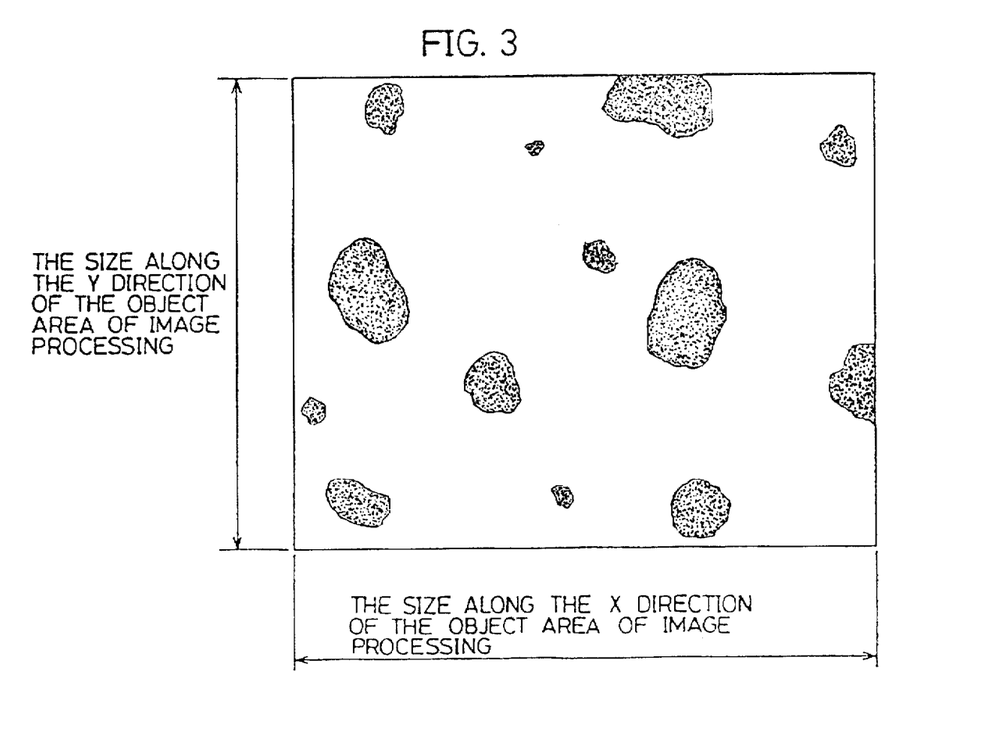
FIG. 3 is an explanatory view showing an example of particle images on a screen of the present invention.

Here, in the particle image screen (frame), it is not possible to calculate accurate circle equivalent diameter and circularity of the particle if the particle image is on the edge of the screen. Therefore, it is necessary to ignore the particle images projected on the edge of the screen. Obviously, larger particles have greater probability of being projected on the edge of the screen, as shown in FIG. 3. This has to be considered in obtaining the correct particle size distribution by an image processing method. The frequency value is, therefore, corrected according to the size of the particle images.

If the particle images are sufficiently small as compared with the capturing area of the video camera 10, the existence area of the barycenters of particle images that are not on the edge of the screen is approximately equal to the capturing area. As the particle images become larger, the existence area of the barycenters of the particle images that are not on the edge of the screen will be narrower as compared with the capturing area.

In other words, the larger the particles are, the less the substantial amount of analyzed samples will be. Accordingly, larger particles have relatively less frequency. The amount of analyzed samples is proportional to the existence area of the barycenters of the particle images that are not on the edge of the screen. Therefore, the particle frequency data of the particles having a circle equivalent diameter in the range of d to (d+Δd) can be corrected by the following formula (5). Namely, the frequency correction coefficient is expressed by $$AS/\{(SX-d) \times (SY-d)\} \qquad (5)$$

wherein AS, SX, and SY are the capturing area of the video camera, the size of the capturing area along the X direction, and the size of the capturing area along the Y direction, respectively. If the capturing area of the video camera is different from the object area of image processing, the above capturing area is replaced by the object area of image processing so as to perform calculation.

Figure 8:
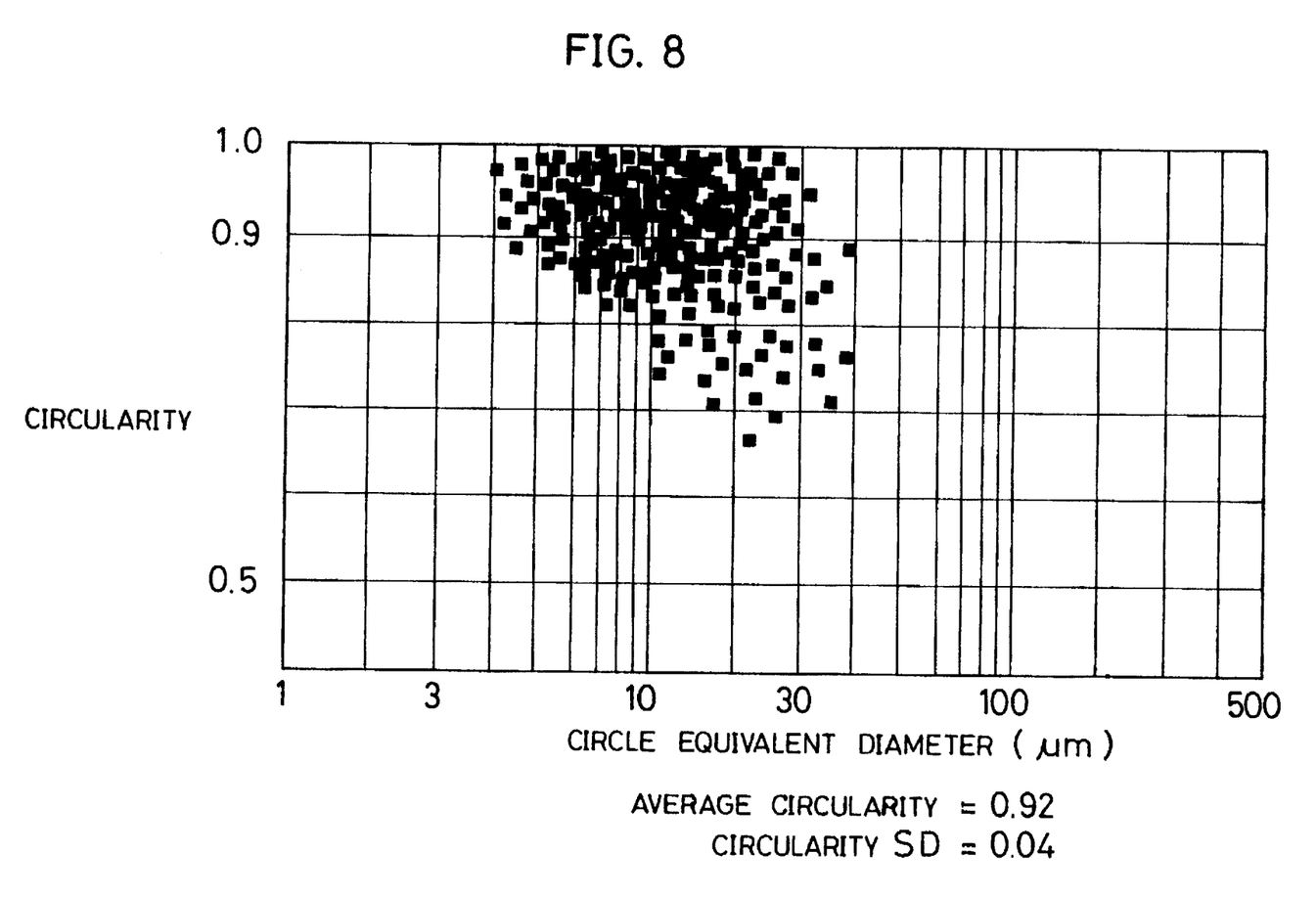
FIG. 8 is an explanatory view showing a display example of a scattergram of the present invention.

First, particle size frequency is independently counted on particle images captured at each magnification. The measuring range of particle diameters at each magnification varies. For example, the measuring range of particle diameters obtained by capturing at a high magnification is set to be 1 to 30 μm, whereas the measuring range of particle diameters obtained by capturing at a low magnification is set to be 15 to 300 μm, as shown in FIG. 8. In this example, the two ranges are allowed to overlap at 15 to 30 μm.

Figure 6:
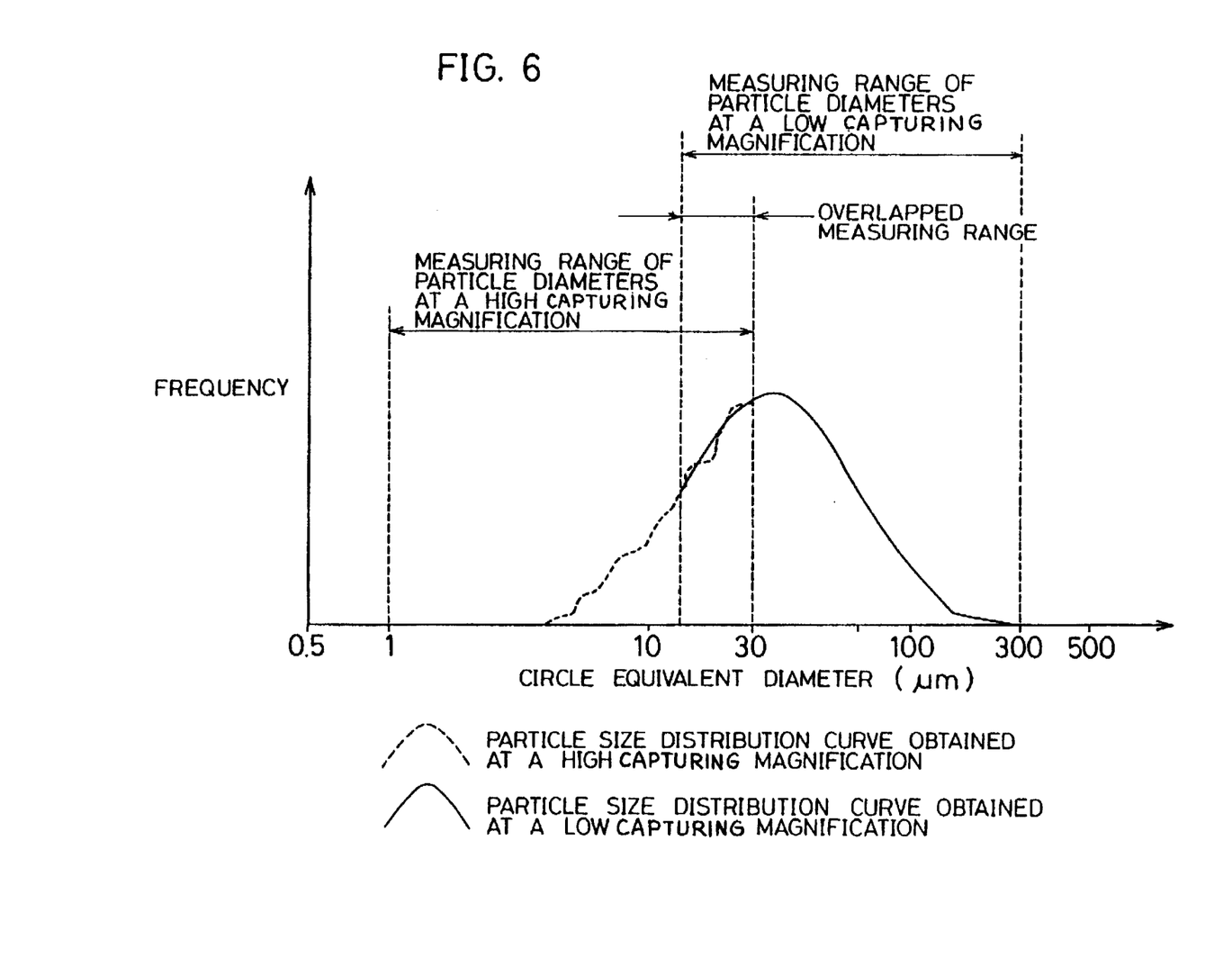
FIG. 6 is a histogram synthesized from two data of different magnifications in capturing images of the present invention.

FIG. 6 shows an example in which the particle diameters vary greatly extending beyond the range of 15 to 30 μm. In such a case, the two particle size frequency data obtained through high magnification capturing and low magnification capturing have to be joined together. In order to achieve this, a frequency correction such as described below is needed depending upon the ratio of the amounts of the analyzed samples obtained through high magnification capturing and low magnification capturing. In the case of low magnification, the capturing area is wide, so that the amount of analyzed samples can generally be increased.

(The corrected frequency at high magnification capturing)=$FH \times AL/AH$ wherein FH, AL, and AH denote the frequency at high magnification capturing, the amount of analyzed samples at low magnification capturing, and the amount of analyzed samples at high magnification capturing, respectively. Here, the amount of analyzed samples can be obtained by the following expression:

(the capturing area)×(the thickness of the particle suspension flow)×(the number of capturing frames)

Even if a frequency correction such as described above is conducted based on the difference in the amounts of analyzed samples, it sometimes happens that the frequency distribution curves obtained from the frequency data do not join together smoothly, causing a step difference at the joining part. This phenomenon occurs often in the case when the frequency distribution curve is extremely uneven as shown by the broken line in FIG. 6 because of the small number of captured particle images due to the low concentration of particles in the suspension.

Another case is that the real amounts of analyzed samples at a high capturing magnification and at a low capturing magnification are different from what is expected because the magnification of the object lens or the projection lens is not what is supposed to be, and therefore the frequency correction based on the above difference in the amounts of analyzed samples is not accurate. However, the problem of step difference due to the inaccurate magnification can be resolved by correcting, in advance, the capturing magnification of each measuring apparatus one by one. According to the apparatus of the present invention, the measuring ranges of particle diameters at different capturing magnifications are allowed to partially overlap with each other and a weighted average of the frequency data obtained from different capturing magnifications is calculated in the overlapped measuring range.

The following method of weighting is employed in calculating the weighted average. As it approaches near the upper limit of the overlapped measuring range, the frequency data obtained at the low magnification capturing is more largely weighted. As it approaches near the lower limit of the overlapped measuring range, the frequency data obtained at the high magnification capturing is more largely weighted. By conducting frequency correction through a method of calculating a weighted average such as above, the frequency distribution data obtained at different magnifications can be smoothly joined together even if the number of captured particle images is small. For example, if the overlapped range at the high and low capturing magnifications is 15 to 30 μm, the particle frequency f(d) with the particle diameters at d to d+Δd (μm) within the overlapped range is calculated by the following formula:

$$f(d)=fh(d)\times(1-(d-15)/(30-15)) + fl(d)\times(1-(30-d)/(30-15))$$

wherein fh(d) and fl(d) denote the particle frequencies with the particle diameters at d to d+Δd (μm) at high and low capturing magnifications, respectively.

Further, the cumulative particle size distribution is calculated based on the particle size frequency data obtained as above. For example, the cumulative particle size data (%) based on the number of particles is calculated by the following formula:

$$FC(d)=NP(d)\times 100/NT$$

wherein FC(d), NP(d), and NT denote the cumulative particle size frequency at particle size d, the number of particles having a particle diameter smaller than d, and the total number of particles, respectively.

Next, a two-dimensional scatter frequency data with two parameters of circle equivalent diameter and circularity is calculated (step S11). In this case also, a two-dimensional frequency data is calculated with respect to each of the high and low capturing magnifications. Then, a frequency correction based on the differences in the size of particle images and a frequency correction based on the differences in the amount of analyzed samples at different capturing magnifications are carried out in the same manner as in the correction processing of the particle size frequency data. Further, a two-dimensional frequency correction in the overlapped measuring range at different capturing magnifications is conducted in the same manner as in the case of joining the above particle size frequency data.

The average particle diameter, standard deviation of the particle diameter, mode diameter, 10% diameter, 50% diameter, 90% diameter, average circularity, standard deviation of the circularity, and others are further calculated using the particle size frequency data, cumulative particle size frequency data, and two-dimensional frequency data of circle equivalent diameter and circularity obtained as above (step S12).

The mode diameter is a particle diameter where the particle size frequency is at its maximum value. The 10% diameter, 50% diameter, and 90% diameter are the particle diameters where the cumulative particle size frequency data is at the values of 10%, 50%, and 90%, respectively. In other words, the 50% diameter is a center value of the particle diameter distribution and is also referred to as the median diameter.

Figure 7:
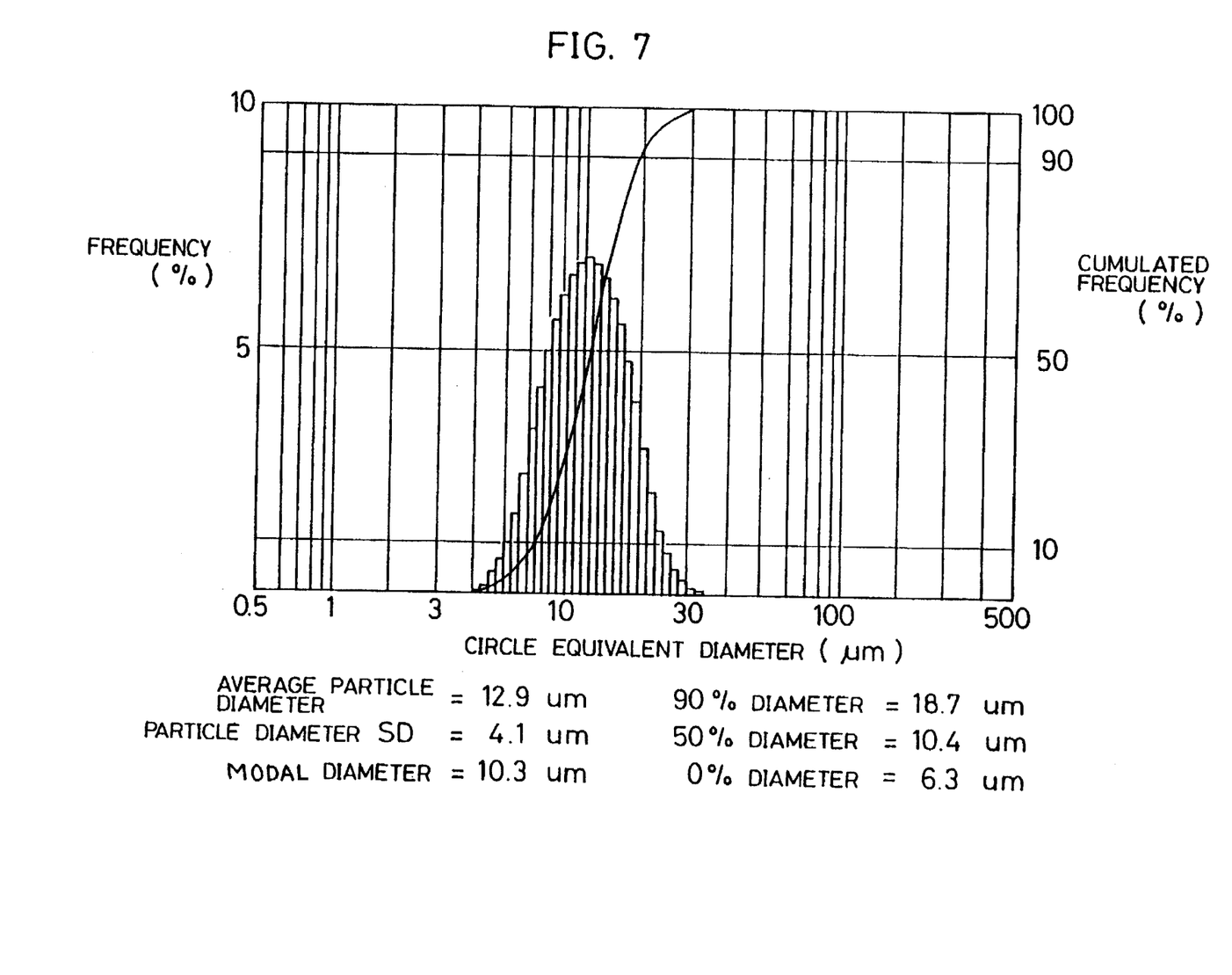
FIG. 7 is an explanatory view showing a display example of particle size distribution and cumulative particle size distribution of the present invention.

As shown in FIGS. 7 and 8, a particle size histogram, a two-dimensional scattergram of circle equivalent diameter and circularity, and the results of analysis such as the average particle diameter and the 50% diameter are displayed based on the frequency data and the results of analysis obtained as above (step S13). In FIG. 7, the axis of abscissa represents the circle equivalent diameter converted to LOG and the axis of ordinate represents both the frequency (%) and the cumulative frequency (%), so that a cumulative particle size distribution curve is displayed as well. In the scattergram display of FIG. 8, the axis of abscissa represents the circle equivalent diameter converted to LOG and the axis of ordinate represents the circularity, where the color of each partition point (dot) is allowed to change in accordance with the two-dimensional frequency value.

Figure 4:
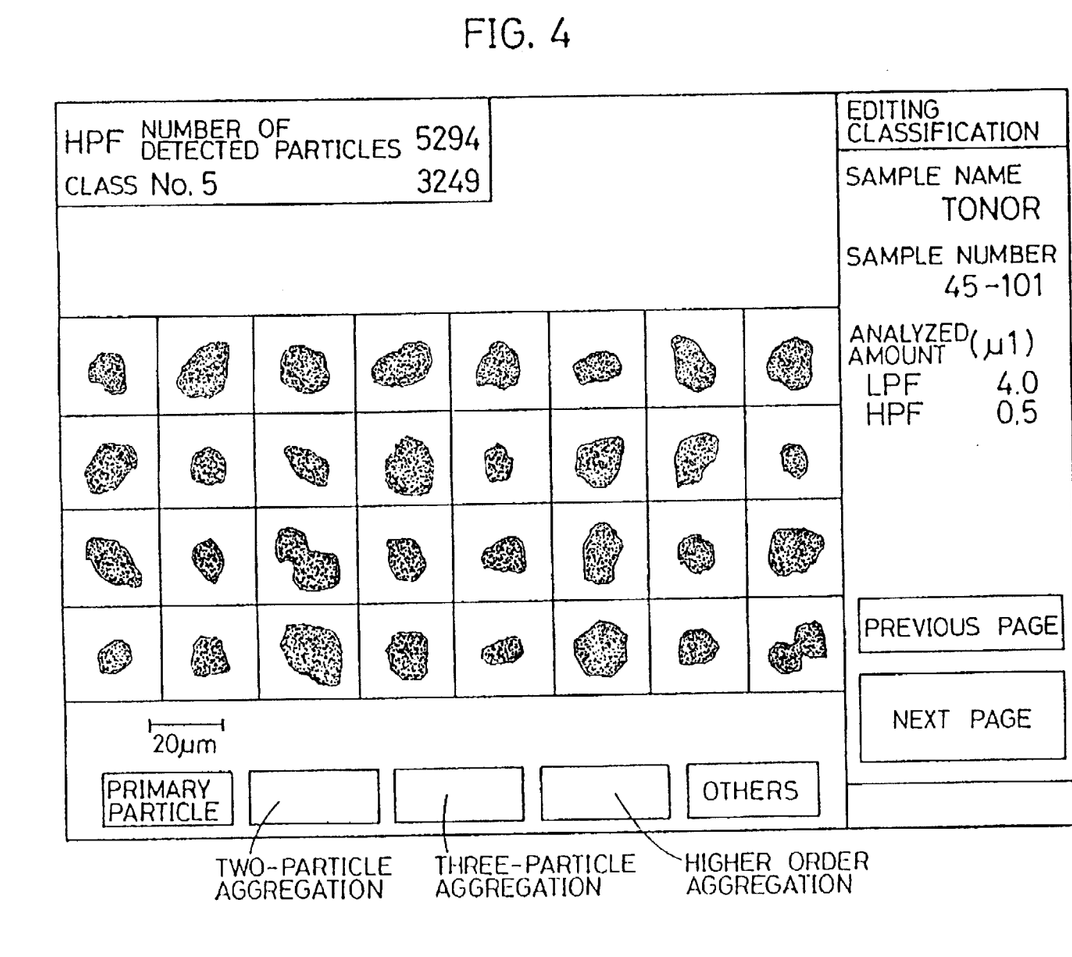
FIG. 4 is an explanatory view showing an example of display images on a monitor television of the present invention.

The apparatus according to the present invention provides functions of not only calculating the circle equivalent diameter and circularity from the particle images captured as above but also storing the captured particle images, classifying them based on their sizes after measurement, and displaying them collectively as shown in FIG. 4. Since the capacity of the image memory for storing the images is limited, it is not possible to store and display all the captured particle images. Since the apparatus is provided with a function of collectively displaying the captured particle images, the user can directly confirm morphological feature and aggregation state of the particles.

If the aggregation of the particles is essential, the user designates and inputs through the keyboard 13 whether the particle image in each of the frames of FIG. 4 is a primary (single) particle image, an aggregated two-particle image, an aggregated three-particle image, an aggregation of higher order, or a particle which is not under consideration. The ratio of the aggregated particles can be automatically calculated based on the result of the above designation. When no aggregated particle images exist in the group of collectively displayed particle images, the calculated circularity of a particle in the above two-dimensional scattergram represents the true circularity of the particle.

Also, it is possible to re-analyze only the primary particle images based on the above result of designation. Since the number of particle images that can be stored is limited, it is sometimes difficult to obtain a result of analysis with good reproducibility. However, by excluding from analysis the aggregated particles and the particles (such as dusts) that are not under consideration, one can obtain a more accurate particle size distribution and circularity.

In the case when the user has confirmed, from the collectively displayed particle images, that the measured particles are spherical, a more accurate particle size distribution can be obtained by re-analyzing only the particles whose circularity is nearly equal to 1 even if the particles are liable to aggregate. Also, when the particles are spherical, one can detect the region where the aggregated particles are distributed in the two-dimensional scattergram of circle equivalent diameter and circularity, as shown in FIG. 9.

Figure 9:
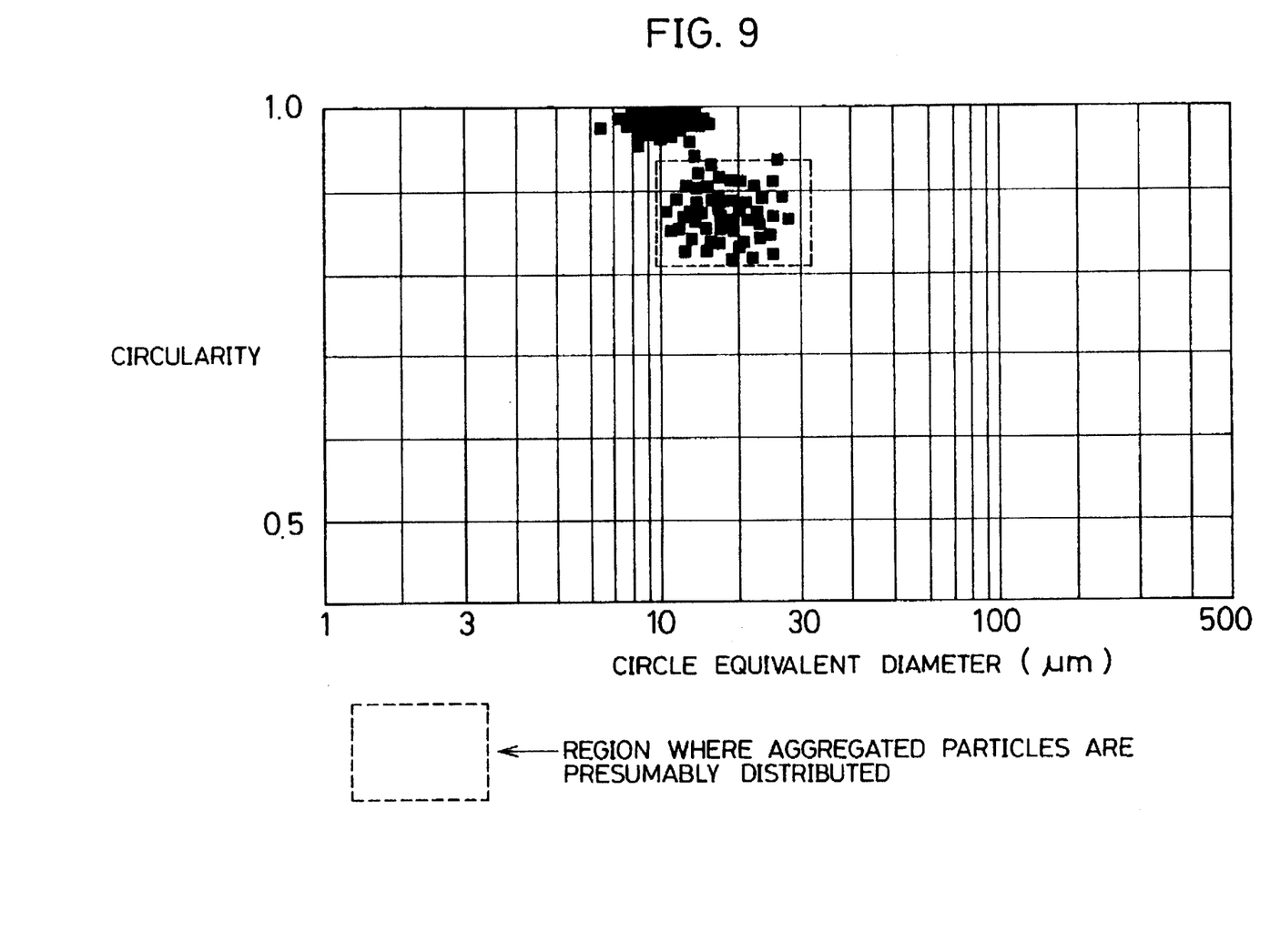
FIG. 9 is an explanatory view showing an example of determining a region in a scattergram of the present invention.

In the example of FIG. 9, the particles that are distributed within the frame drawn by the dotted lines are presumed to be aggregated particles. When two or three spherical particles having approximately the same diameter are aggregated, the projected area of the particle images will be large, so that their circle equivalent diameter will be about $\sqrt{2}$ times or $\sqrt{3}$ times larger and the circularity will be as small as 0.9 or less. One can obtain an index for the degree of particle aggregation by counting the number of particles within the frame drawn by the dotted lines.

In the present apparatus, the user can take up a certain two-dimensional region in the two-dimensional scattergram of circle equivalent diameter and circularity and conduct particle size analysis and circularity analysis on only the particles which are located either within or outside the region, as shown in the example of FIG. 9. By making use of such a function as described above, one can obtain particle size distribution and average circularity based on the data excluding the dusts and aggregated particles. One can also determine the ratio of the aggregated particles. Through the keyboard 13, a mouse, or any other input device the user can arbitrarily select or change such two-dimensional regions depending on the kind of samples to be measured.

As described above, according to the flow-type particle image analyzing apparatus of the present invention, the user can not only confirm the particle images directly by eye-inspection but also obtain quantitative information, namely new information such as circularity and degree of aggregation, which was not available by a measuring apparatus employing a conventional electric detection zone method or laser analysis scattering method. Also, the user can detect a distribution region of dusts and aggregated particles in the sample by use of a two-dimensional scattergram of circle equivalent diameter and circularity, so that the user can obtain a more accurate particle size distribution by conducting a particle size analysis excluding the particle data within the region.

The present invention provides the following effects.

1. By conducting an image analysis of particle images, one can obtain information on not only the particle size (circle equivalent diameter) but also the perimeter and circularity of the particle image.
2. The particle suspension flow is hydrodynamically transformed into a narrow or flat flow by a sheath liquid, so that the position through which the barycenter of each of the particles passes is, irrespective of the size of the particles, almost invariable with respect to the capturing direction. Therefore, particle images are always captured in focus, enabling the user to obtain a more reliable result of measurement than in the case of conventional microscope image processing method.
3. Since the particle suspension flow is hydrodynamically transformed into a narrow or flat sample flow, flat particles and oblong particles tend to arrange themselves in order, so that the circle equivalent diameter and circularity obtained from particle images have small differences, which leads to good reproducibility.
4. Since the particle images that are captured and stored can be, after measurement, collectively displayed on a display, it is possible to confirm morphological feature and aggregation state of the particles without difficulty.
5. By examining the particle images that are captured and stored, the user can differentiate, by eye inspection, whether the particles are aggregated or not, so that the user can classify the particles and obtain the ratio of the aggregated particles.
6. In the case when the particles have been, from the collectively displayed particle images, confirmed to be spherical, a more accurate particle size distribution can be obtained by analyzing only the particles whose circularity is nearly equal to 1 even if the particles are liable to aggregate.
7. If the particles have been, from the collectively displayed particle images, confirmed to be spherical, one can obtain an index for the degree of particle aggregation from the two-dimensional scattergram of circle equivalent diameter and circularity.

What is claimed is:

1. An apparatus for analyzing particle images comprising:
   a sheath flow cell for transforming a flow of particle suspension into a flow surrounded by a sheath liquid;
   irradiating means for irradiating particles in the transformed particle suspension flow with a light;
   image capturing means for capturing particle images of the irradiated particles;
   image analyzing means for analyzing the captured particle images; and
   a display,
   the image analyzing means including:
   calculating means for measuring a projected area of each captured particle image to calculate a particle diameter of each particle;
   graph making means for making a histogram based on particle size frequency data corresponding to the particle diameters and for allowing the display to display the histogram;
   storage means for storing each captured particle image; and
   particle image recalling means for allowing the display means to collectively display the particle images stored by the storage means,
   wherein the image capturing means further includes means for providing a plurality of capturing magnifications, wherein measuring ranges of particle diameters differ at each capturing magnification and partially overlap each other,
   wherein the calculating means calculates particle size frequency data based on particle images captured at the plurality of capturing magnifications, corrects the particle size frequency data depending upon an amount of samples obtained at each capturing magnification, and integrates the particle size frequency data obtained at the plurality of capturing magnifications.

2. The apparatus according to claim 1, which further comprises at least one of supply means for selecting a sheath liquid from plural kinds of sheath liquid in accordance with a property of the particle suspension to supply the selected sheath liquid to the sheath flow cell and dyeing means for staining the particles in advance.

3. The apparatus according to claim 1, wherein the sheath flow cell transforms the particle suspension flow into a flat flow and the image capturing means captures images of the particles through a flat surface of the particle suspension flow.

4. The apparatus according to claim 1, wherein the calculating means and the graph making means ignore the particle images that are on an edge of a screen obtained by the image capturing means to obtain the particle size frequency data and correct the obtained frequency data according to the particle diameter.

5. The apparatus according to claim 1, wherein the calculating means further includes means for measuring a perimeter of each captured particle image to calculate a circularity of each particle and the graph making means further includes means for making a scattergram based on two parameters corresponding to the particle diameter and the circularity and for allowing the display to display the scattergram.

6. The apparatus according to claim 1, wherein the calculating means integrates, by weighted average method, the particle size frequency data obtained at the plurality of capturing magnifications.

7. A method for analyzing particle images comprising the steps of:
   transforming a flow of particle suspension into a flow surrounded by a sheath liquid;
   irradiating particles in the transformed particle suspension flow with a light;
   capturing particle images of the irradiated particles, said capturing step including providing a plurality of capturing magnifications, wherein measuring ranges of particle diameters differ at each capturing magnification and partially overlap each other;
   analyzing the captured particle images, including
   measuring a projected area and perimeter of each captured particle image;
   calculating a particle diameter of each particle in accordance with the measuring step, said calculating step including determining particle size frequency data based on particle images captured at the plurality of capturing magnifications, correcting the particle size frequency data depending upon an amount of samples obtained at each capturing magnification, and integrating the particle size frequency data obtained at the plurality of capturing magnifications, and making a histogram based on particle size frequency data corresponding to the particle diameters;

displaying the histogram and the scattergram;

storing each captured particle image; and collectively displaying the particle images stored by the storing means, the collective displaying providing confirmation of morphology and aggregation of the irradiated particles.

8. The method according to claim 7, wherein the analyzing step further includes measuring a perimeter of each captured particle image to calculate a circularity of each particle and making a scattergram based on two parameter corresponding to the particle diameter and the circularity, and the displaying step further includes displaying the scattergram.

9. The method according to claim 8, wherein said analyzing step includes calculating, from the calculated circularity of each particle, at least one of circularity frequency data, an average of circularity, and a standard deviation of circularity to be displayed by the displaying step.

10. The method according to claim 7, wherein the integrating step includes integrating, by weighted average method, the particle size frequency data obtained at the plurality of capturing magnifications.

11. The method according to claim 7, further comprising selecting a sheath liquid from plural kinds of sheath liquid in accordance with a property of the particle suspension;

supplying the selected sheath liquid to the sheath flow cell; and staining the particles in advance.

12. The method according to claim 7, wherein said transforming step includes transforming the particle suspension flow into a flat flow and the capturing step includes capturing images of the particles through a flat surface of the particle suspension flow.

13. The method according to claim 12, wherein the calculating step further includes:

calculating particle size frequency data based on particle images capture at the plurality of capturing magnifications, correcting the particle size frequency data depending upon an amount of samples obtained at each capturing magnification, and smoothly integrating, by a weighted average method, the particle size frequency data obtained at the plurality of capturing magnifications.

14. The method according to claim 7, wherein the calculating step and the making steps each further include ignoring the particle images that are on an edge of a screen obtained by the capturing step to obtain the particle size frequency data and correcting the obtained frequency data according to the particle diameter.

15. The method according to claim 7, wherein the capturing step further includes providing a plurality of capturing magnifications, wherein measuring ranges of particle diameters differ at each capturing magnification and partially overlap each other.

16. The method according to claim 7, wherein the analyzing step further includes:

inputting information as to whether each of the collectively displayed particle images represents a single particle or an aggregation of a plurality of particles;

calculating a numerical proportion of the single particles to the aggregations based on the input information; and outputting the calculated proportion.

17. The method according to claim 7, wherein the analyzing step further includes inputting information as to whether each of the collectively displayed particle images represents a single particle or an aggregation of a plurality of particles, and the calculating step further includes calculating the particle diameter and circularity of the particle based only on the images of the single particles differentiated by the input information.

18. An apparatus for analyzing particle images comprising:

a sheath flow cell for transforming a flow of particle suspension into a flow surrounded by a sheath liquid;

irradiating means for irradiating particles in the transformed particle suspension flow with a light;

image capturing means for capturing particle images of the irradiated particles;

image analyzing means for analyzing the captured particle images, the image analyzing means including:

means for providing a plurality of capturing magnifications, wherein measuring ranges of particle diameters differ at each capturing magnification and partially overlap each other, and calculating means for calculating particle size frequency data based on particle images captured at the plurality of capturing magnifications, correcting the particle size frequency data depending upon an amount of samples obtained at each capturing magnification, and integrating the particle size frequency data obtained at the plurality of capturing magnifications.

19. The apparatus according to claim 18, wherein the calculating means integrates, by a weighted average method, the particle size frequency data obtained at the plurality of capturing magnifications.

20. An apparatus for analyzing particle images comprising:

a sheath flow cell for transforming a flow of particle suspension into a flow surrounded by a sheath liquid;

irradiating means for irradiating particles in the transformed particle suspension flow with a light;

image capturing means for capturing particle images of the irradiated particles;

image analyzing means for analyzing the captured particle images, the image analyzing means including:

storage means for storing each captured particle image, particle image recalling means for allowing a display to collectively display the particle images stored by the storage means, input means for inputting information as to whether each of the collectively displayed particle images represents a single particle or an aggregation of a plurality of particles, means for calculating a numerical proportion of the single particles to the aggregations based on the input information, and means for outputting the calculated proportion.

21. The apparatus according to claim 20, wherein the image analyzing means further includes operating means for calculating, from the calculated circularity of each particle, at least one of circularity frequency data, an average of circularity, and a standard deviation of circularity to be displayed by the display.

22. The apparatus according to claim 20, wherein the image analyzing means further includes input means for inputting information as to whether each of the collectively displayed particle images represents a single particle or an aggregation of a plurality of particles, and means for calculating a numerical proportion of the single particles to the aggregations based on the input information to allow the display means to display the calculated proportion.

23. The apparatus according to claim 20, wherein the image analyzing means further includes input means for inputting information as to whether each of the collectively displayed particle images represents a single particle or an aggregation of a plurality of particles, and the calculating means calculates the particle diameter and circularity of the particle based only on the images of the single particles differentiated by the input information.

24. An apparatus for analyzing particle images comprising:

a sheath flow cell for transforming a flow of particle suspension into a flow surrounded by a sheath liquid;
irradiating means for irradiating particles in the transformed particle suspension flow with a light;
image capturing means for capturing particle images of the irradiated particles;
image analyzing means for analyzing the captured particle images, the image analyzing means including:
  storage means for storing each captured particle image,
  particle image recalling means for allowing a display to collectively display the particle images stored by the storage means,
  input means for inputting information as to whether each of the collectively displayed particle images represents a single particle or an aggregation of a plurality of particles, and
  calculating means for calculating the particle diameter and circularity of the particle based only on the images of the single particles differentiated by the input information.

* * * * *